(12) United States Patent
Dutt et al.

(10) Patent No.: US 10,772,879 B2
(45) Date of Patent: *Sep. 15, 2020

(54) PHARMACEUTICAL FORMULATIONS

(71) Applicant: TORRENT PHARMACEUTICALS LIMITED, Ahmedabad (IN)

(72) Inventors: Chaitanya Dutt, Gandhinagar (IN); Jaya Abraham, Gandhinagar (IN); Vivek Mishra, Gandhinagar (IN); Amit Kesarwani, Gandhinagar (IN); Ramesh Chandra Gupta, Gandhinagar (IN); Shailesh Deshpande, Gandhinagar (IN); Shital Kumar Zambad, Gandhinagar (IN); Anoop Mathur, Gandhinagar (IN); Jignesh Kotecha, Gandhinagar (IN); Sachin Latad, Gandhinagar (IN); Manish Patel, Gandhinagar (IN); Anita Chaudhari, Gandhinagar (IN)

(73) Assignee: Torrent Pharmaceuticals Limited, Gujarat, Ahmedabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/564,720

(22) PCT Filed: Apr. 5, 2016

(86) PCT No.: PCT/IB2016/051920
§ 371 (c)(1),
(2) Date: Oct. 5, 2017

(87) PCT Pub. No.: WO2016/162787
PCT Pub. Date: Oct. 13, 2016

(65) Prior Publication Data
US 2018/0110763 A1    Apr. 26, 2018

(30) Foreign Application Priority Data
Apr. 8, 2015 (IN) .......................... 1475/MUM/2015

(51) Int. Cl.
*A61K 31/4436* (2006.01)
*A61K 47/54* (2017.01)
*A61K 47/12* (2006.01)
*A61K 47/02* (2006.01)
*A61P 3/10* (2006.01)
*A61K 9/00* (2006.01)
*A61K 9/20* (2006.01)

(52) U.S. Cl.
CPC ........ *A61K 31/4436* (2013.01); *A61K 9/0095* (2013.01); *A61K 9/2009* (2013.01); *A61K 9/2013* (2013.01); *A61K 9/2054* (2013.01); *A61K 47/02* (2013.01); *A61K 47/12* (2013.01); *A61K 47/541* (2017.08); *A61P 3/10* (2018.01)

(58) Field of Classification Search
CPC .. A61K 31/4436; A61K 47/02; A61K 47/541; A61K 47/12; A61P 3/10
See application file for complete search history.

(56) References Cited

U.S. PATENT DOCUMENTS

2011/0034378 A1 * 2/2011 Dutt .................. A61K 31/00
514/6.5

FOREIGN PATENT DOCUMENTS

| EP | 1222171 A1 | 7/2002 | |
| EP | 1222171 B1 * | 2/2004 | ......... A61K 31/4425 |

OTHER PUBLICATIONS

Krug et al. Biomaterials, V.34, p. 275-282.*
International Search Report for corresponding Application No. PCT/IB2016/051920 dated on Jul. 8, 2016.

* cited by examiner

*Primary Examiner* — Yong L Chu
(74) *Attorney, Agent, or Firm* — Melissa M. Hayworth; E. Joseph Gess

(57) ABSTRACT

This invention relates to pharmaceutical formulations comprising 1-(2-thien-2'-yl-2-oxo-ethyl)-3-(methanesulfonyl hydrazine carbonyl) pyridinium, its pharmaceutically acceptable salts, salt-cocrystals and co-crystals, particularly 1-(2-thien-2'-yl-2-oxo-ethyl)-3-5(methanesulfonyl hydrazine carbonyl) pyridinium chloride. The formulations are suitable for oral administration and also comprise a permeability enhancer or a suitable base or a mixture thereof. The formulations of this invention are for treating diseases associated with advanced glycation end products.

24 Claims, No Drawings

PHARMACEUTICAL FORMULATIONS

FIELD OF THE INVENTION

This invention relates to pharmaceutical formulations comprising 1-(2-thien-2'-yl-2-oxo-ethyl)-3-(methanesulfonyl hydrazine carbonyl) pyridinium, its pharmaceutically acceptable salts, salt-cocrystals and co-crystals, particularly 1-(2-thien-2'-yl-2-oxo-ethyl)-3-(methanesulfonyl hydrazine carbonyl) pyridinium chloride. The formulations are suitable for oral administration and also comprise a permeability enhancer or a suitable base or a mixture thereof. The formulations of this invention are for treating diseases associated with advanced glycation end products selected from diabetic and aging-related macrovascular and microvascular complications including, heart failure, nephrological disorder, neuropathy, atherosclerosis and retinal disorder; dermatological disorder, endothelial or other organ dysfunction and growth impairment.

BACKGROUND

Maillard in 1912 found that reducing sugars, such as glucose and ribose react with proteins to form brown pigments. Further studies have shown that this is an irreversible non-enzymatic reaction, which occurs in several natural systems including stored foodstuff. The Maillard reaction occurs in two stages, early and advanced. Initially, proteins react with glucose to form stable Amadori products, which subsequently cross-links to form advanced glycation end products (AGE). In most cases, the formation of AGE also accompanies browning of the proteins and increase in the fluorescence.

In diabetes, where blood glucose level is significantly higher than normal, the reaction of glucose with several proteins such as hemoglobin and collagen, gives rise to the formation of AGE, which in turn, is responsible for the complications associated with diabetes, such as nephropathy, microangiopathy, endothelial dysfunction and other organ dysfunctions. In addition, the activity of several growth factors, such as basic fibroblast growth factor, is also impaired. AGE products, unlike normal proteins in tissue, have a slower rate of turnover and replenishment. It has been reported that AGE products may in fact elicit a complex immunological reaction involving RAGE (Receptor for Advanced Glycation End Products) and activation of several incompletely defined immunological processes. (Stehouwer et al; *Cardiovascular Research* 1997; 34:55-68 and Smit et al; *Current Medicinal Chemistry* 2004; 11:2767-84).

Due to the clinical significance of AGE formation, several successful therapeutic approaches have been tried based upon intervening in the accumulation of AGEs in vivo. One of the approaches is to inhibit the formation of AGEs from its precursors, by the administration of therapeutic agents. In another approach for controlling levels of AGEs in tissues, therapeutic agent is administered which can reverse or break AGE cross-links, especially in those tissues in which AGE cross-links have already accumulated to levels which are responsible for subclinical or clinical pathology.

1-(2-thien-2'-yl-2-oxo-ethyl)-3-(methanesulfonyl hydrazine carbonyl) pyridinium and its pharmaceutically acceptable salts is one of a class of compounds which have been shown to have AGE breaking activity (EP1222171; EP1243581).

1-(2-thien-2'-yl-2-oxo-ethyl)-3-(methanesulfonyl hydrazine carbonyl) pyridinium chloride has been shown to improve cardiomyopathy and nephropathy in animal models of Type II diabetes (Joshi et al; *J. Cardiovasc. Pharmacol.*; 2009, 54(1): 72-81). Clinical studies have shown this compound to be safe and well tolerated when administered orally (Chandra et al; *Clin. Drug. Invest.*; 2009, 29(9): 559-575).

However, it was noted that bioavailability of 1-(2-thien-2'-yl-2-oxo-ethyl)-3-(methanesulfonyl hydrazine carbonyl) pyridinium compounds, for example, 1-(2-thien-2'-yl-2-oxo-ethyl)-3-(methanesulfonyl hydrazine carbonyl) pyridinium bromide was very low, when administered orally to rats. (Data on file)

Further, phase I clinical studies have also revealed that the oral bioavailability of 1-(2-thien-2'-yl-2-oxo-ethyl)-3-(methanesulfonyl hydrazine carbonyl) pyridinium chloride is very low (Chandra et al; *Clin. Drug. Invest.*; 2009, 29(9): 559-575); and high doses (more than 1000 mg bid) are therefore required in order to achieve therapeutically effective response in humans.

It is an aim of certain embodiments of this invention to provide a pharmaceutical formulation of 1-(2-thien-2'-yl-2-oxo-ethyl)-3-(methanesulfonyl hydrazine carbonyl) pyridinium, its pharmaceutically acceptable salts, salt-cocrystals and co-crystals. It is an aim of certain embodiments to provide formulations which deliver a therapeutically effective amount of 1-(2-thien-2'-yl-2-oxo-ethyl)-3-(methanesulfonyl hydrazine carbonyl) pyridinium its pharmaceutically acceptable salts, salt-cocrystals and co-crystals orally. It is an aim of certain embodiments to provide formulations which exhibit an increased oral bioavailability of 1-(2-thien-2'-yl-2-oxo-ethyl)-3-(methanesulfonyl hydrazine carbonyl) pyridinium compound relative to prior art formulations. Certain embodiments of the invention achieve some or all of the above aims.

SUMMARY OF THE INVENTION

In a first aspect of the present invention is provided an oral pharmaceutical formulation comprising:
a compound of formula (I):

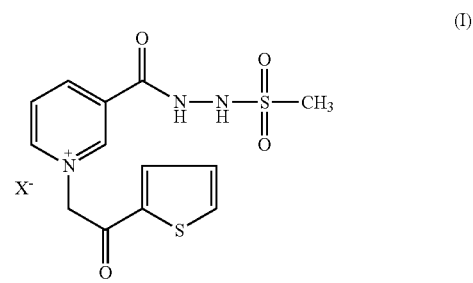

or its co-crystal; wherein X⁻ is a pharmaceutically acceptable anion or X⁻ is absent;
a permeability enhancing agent or a base or a mixture thereof;
and optionally other pharmaceutically acceptable excipients.

The inventors have recognised that compounds of formula (I) are mainly absorbed through upper GI tract. It was observed that though oral bioavailability of compound of formula (I) is very less, it increases substantially in presence of a permeation enhancer or a base. The inventors have further found that adding a base or a buffer in combination with a permeability enhancing agent further boosts the oral bioavailability of the compounds of formula (I).

The inventors have shown that compounds of formula (I) associate well with permeability enhancing agents (e.g. sodium caprate) at high pH but not at low pH, specifically at pH below 2.0. It is therefore suggested (without wishing to be bound by theory) that the presence of a base or buffer in the formulation allows the formation in the upper GI tract of a suitable microenvironment in the vicinity of the compound of formula (I) and the permeability enhancing agent. In that microenvironment, the pH is maintained at a sufficiently high level, preferably more than 2, to allow the permeability enhancing agent to aid the absorption of the compound of formula (I), thus boosting of bioavailability is observed in comparison to the formulation when either of permeability enhancer or base is used.

$X^-$ may be a halide ion. $X^-$ may be selected from chloride and bromide. Preferably, $X^-$ is $Cl^-$.

$X^-$ may be a carboxylate anion, e.g. a $C_2$-$C_{20}$ carboxylate anion. $X^-$ may thus be caprate. Where $X^-$ is a carboxylate anion (e.g. caprate), it may be that $X^-$ is the permeability enhancing agent. In this embodiment, there may be no other permeability enhancing agent. In other words, the counter ion may act as the permeability enhancing agent and no other permeability enhancing agent is required. Though an additional one may be provided separately if desired and this additional permeability enhancing agent may or may not comprise the same anion as $X^-$.

The compounds of formula (I) in the formulation may have different counter ions. In other words the active ingredient may be presented with a mixture of two or more counter ions.

Thus it may be that a portion of the compounds of formula (I) have one counter ion and the remaining compounds of formula (I) have a different counter ion. Thus it may be that in a portion of the compounds of formula (I) in the formulation $X^-$ is chloride and in the remaining compounds of formula (I) $X^-$ is caprate.

When $X^-$ absent, compound of formula (I) may exist in ylide form.

In certain preferred embodiments, the formulation comprises:
  a compound of formula (I):

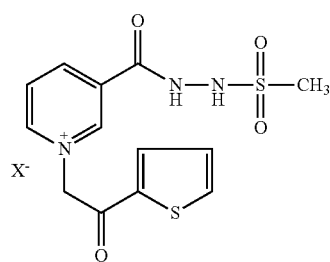

(I)

or its co-crystal; wherein $X^-$ is a pharmaceutically acceptable anion or $X^-$ is absent;
  a permeability enhancing agent and a base;
  and optionally other pharmaceutically acceptable excipients.

The compound of formula (I) or its co-crystal may be present in an amount from about 0.1% to about 80% w/w of total formulation, preferably in an amount from about 0.25% to about 70% w/w of total formulation, and most preferably in an amount from about 5% to about 50% w/w of total formulation.

A "permeability enhancing agent" or "permeability enhancer" is a compound which increases the rate of transportation of drugs across biomembranes. Permeability enhancing agent according to present invention is pharmaceutically acceptable.

Permeability enhancing agent according to present invention may be selected from:
  1) Surfactants. Examples include poly oxyethylene ethers, poly oxyethylene esters, poly oxyethylene sorbitan esters, dodecylmaltoside and the like;
  2) Fatty Acids. Examples include cholic acid (CA), hexanoic acid (HA) and heptanoic acid (HPA), lipoic acid, caprylic acid, palmitic acid, linoleic acid, tetradecanoic acid (myristic acid) and the like;
  3) Salts of Fatty acids. Examples include sodium caprylate, sodium caprate, sodium laurate and sodium oleate (SOA) and the like;
  4) N-Acylated α-Amino Acids and N-Acylated Non-α-Amino Acids. Examples include N-cyclohexanoylleucine, N-(phenylsulphonyl) leucine and the like;
  5) Saponins. Example include glycyrrhizinate;
  6) Bile Salts. Examples include chenodeoxycholate, ursodeoxycholate;
  7) Medium Chain Triglycerides. Examples include caprylic/capric triglyceride, glyceryl tricaprylate/caprate and the like;
  8) Polymers. Examples include polyoxylene alkyl ethers, polycarbophil (acrylic acid polymer), chitosan, carbopol, pyrrolidine and the like;
  9) Acylcarnitines and Alkanoylcholins. Examples include palmitoyl-DL-carnitine chloride (PCC);
  10) Secretory Transport Inhibitors. Examples include Polysorbate 80, polyoxyethylene alkyl ethers (e.g. Cremophor EL™), poloxamers (e.g. Pluronic™, Lutrol™) and the like;
  11) Thiolated polymers-thiomers: Examples include polycarbophyl polymer with covalent attachment of cysteine (PCP-Cys), sodium carboxymethylcellulose-cystine, chitosan-cysteine, chitosan-4-thio-butylamidine and the like;
  12) Complexation agents: Examples include ethylene diamine tetra acetate, hydroxypropyl betadex, cyclodextrin and the like,
  or combinations thereof.

It may be that each permeability enhancing agent is selected from those permeability enhancing agents which are a salt comprising a metal cation and an organic anion.

It may be that permeability enhancing agent is a $C_2$-$C_{20}$ carboxylic acid or metal salt or an ammonium salt or an ester of a $C_2$-$C_{20}$ carboxylic acid. It may be a $C_8$-$C_{12}$ carboxylic acid or metal salt or an ammonium salt or an ester of a $C_8$-$C_{12}$ carboxylic acid. It may be a $C_{10}$ carboxylic acid or metal salt or an ammonium salt or ester of a $C_{10}$ carboxylic acid. The carboxylic acid may be saturated or the carboxylic acid may be unsaturated. Preferably, the permeability enhancing agent is a metal salt of capric acid. The metal salt of a carboxylic acid may be an alkali metal salt, an alkaline earth metal salt or combinations thereof. The metal salt may be an alkali metal salt, e.g. a potassium salt or a sodium salt. Preferably, it is a sodium salt.

Preferably, the permeability enhancing agent is sodium caprate.

It may be that the compound of formula (I) and the permeability enhancing agent (e.g. sodium caprate) are in the form of a conjugate. It is equally within the scope of this invention that they are not in the form of a conjugate or associated in any way other than both being present in the formulation.

The permeability enhancing agent when present, it may be in an amount from about 0.02% to about 75% w/w of total formulation, preferably in an amount from about 2.5% to about 60% w/w of total formulation, and most preferably in an amount from about 5% to about 30% w/w of total formulation.

Base or buffer according to present invention are interchangeable and may be any agent which increases the pH of any aqueous medium above 2, to which it is added. According to present invention, base or buffer is pharmaceutically acceptable.

Base may be an organic base. An organic base is generally an organic compound comprising at least one nitrogen atom having a free lone pair. Common basic functional groups include amines (including primary amines, secondary amines and tertiary amines), guanidines, pyridines, imidazoles etc. Organic bases suitable for use in oral pharmaceutical formulations are often basic amino acids and carbohydrates. Examples of basic amino acids include arginine, lysine and histidine. Examples of basic carbohydrates include meglumine and glucosamine.

Base may be a salt of a carboxylic acid, e.g. a metal salt or an ammonium salt of a carboxylic acid. The carboxylic acid may comprise a single carboxylate group or two carboxylate groups. The carboxylic acid (whether it has one or two carboxylate groups) may comprise less than 5 carbons atoms. Examples of ammonium salts include ammonium acetate and ammonium formate. The base may be a metal acetate. The metal may be an alkali metal or an alkaline earth metal. The metal may be selected from sodium, calcium, magnesium and potassium. Examples of metal salts of carboxylic acids include sodium acetate and potassium propanoate. Where the carboxylic acid comprises two carboxylate groups it may be that both carboxylate groups are in the form of a metal salt or it may be that one carboxylate group is in the form of a metal salt and the other is in the form of a carboxylic acid.

Where the base is a salt of a carboxylic acid, the carboxylic acid may also be present in the formulation.

Alternatively, the base may be an inorganic base. Suitable inorganic bases include ammonium of metal hydroxides, carbonates and bicarbonates. Examples of ammonium salts include ammonium hydroxide. The metal may be an alkali metal or an alkaline earth metal. Thus the base may be an alkali metal or alkaline earth metal carbonate or bicarbonate. The metal may be selected from sodium, calcium, magnesium and potassium. The base may be an alkaline earth metal carbonate or bicarbonate. It may be an alkaline earth metal carbonate. Examples of inorganic bases include sodium carbonate, sodium bicarbonate, potassium carbonate, potassium bicarbonate, calcium carbonate, magnesium carbonate, magnesium bicarbonate. In certain preferred embodiments, the base is magnesium carbonate.

The base may be a phosphate buffer.

The base when present, it may be in an amount from about 0.002% to about 60% w/w of total formulation, and preferably in an amount from about 0.2% to about 25% w/w of total formulation, more preferably from about 0.5% to about 15.0% w/w of total formulation, and most preferably from about 0.5% to about 5.0% w/w of total formulation.

In certain preferred embodiments, the formulation comprises:

Compound of formula Ia or Ia':

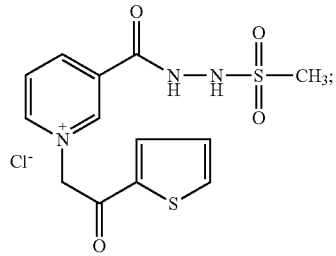

Ia

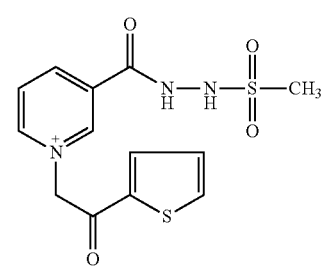

Ia' or its co-crystal
an alkali metal salt of a $C_8$-$C_{12}$ carboxyllic acid (e.g. sodium caprate), or
a base or a mixture thereof; and
optionally other pharmaceutically acceptable excipients.

Dosage levels, dose frequency, and treatment durations with formulation of the invention are expected to differ depending on the formulation and clinical indication, age, and co-morbid medical conditions of the patient. Preferably, however, the formulation is for administration once daily or twice daily, preferably twice daily. Each formulation or formulations according to present invention may comprise from 100 mg to 2000 mg of the compound of formula (I) (e.g. compound Ia or Ia' or its co-crystal). Each formulation may comprise from 150 mg to 1500 mg of the compound of formula (I) (e.g. compounds Ia or Ia' or its co-crystal). Preferably, the each formulation comprises from 250 mg to 750 mg of the compound of formula (I) (e.g. compounds Ia or Ia' or its co-crystal).

The formulation may be for use in treating, preventing or managing a disease selected from: diabetes and aging related macrovascular and microvascular complications including heart failure, nephrological disorder, neuropathy, atherosclerosis and retinal disorder; dermatological disorder, endothelial or other organ dysfunction and growth impairment.

The invention also provides a method of treating, managing or preventing a complication associated with aging and diabetes; the method comprising administering to a subject in need thereof an oral pharmaceutical formulation comprising compound of Formula (I), Ia or Ia' or its co-crystals as described above, in a therapeutically effective amount.

The invention also provides a method of treating, managing or preventing a disease selected from: diabetes and aging related macrovascular and microvascular complications including, heart failure, nephrological disorder, atherosclerosis and retinal disorder; dermatological disorder, endothelial or other organ dysfunction and growth impairment; the method comprising administering to a subject in need thereof an oral pharmaceutical formulation comprising compound of Formula (I), Ia or Ia' or its co-crystals as described above, in a therapeutically effective amount.

In a second aspect is provided a conjugate of a compound of formula (I) and a permeability enhancing agent. Where appropriate (i.e. where they pertain to the identity of the permeability enhancing agent and the compound of formula (I)), the embodiments described above for the formulations of the first aspect apply equally to the conjugates of the second aspect. Thus, the conjugate may be a conjugate of compound Ia or Ia' and sodium caprate.

Preferably, formulations comprising conjugate of a compound of formula (I), Ia or Ia' and a permeability enhancing agent may further comprises a permeability enhancer or a base or a mixture thereof and optionally other pharmaceutically acceptable excipients.

DETAILED DESCRIPTION OF THE INVENTION

In their simplest form, the formulations of the invention comprise only the compound of formula (I), Ia or Ia' or in association of permeability enhancer or base or a mixture thereof. However, the formulations of the invention will generally also comprise at least one other pharmaceutically acceptable excipient (e.g. at least one other adjuvant, diluent or carrier). Conventional procedures for the selection and preparation of suitable pharmaceutical formulations are described in, for example, "Pharmaceuticals—The Science of Dosage Form Designs", M. E. Aulton, Churchill Livingstone, 1988 or *Handbook of pharmaceutical excipients* (*sixth edition*, 2009).

The oral pharmaceutical formulation as described herein may be obtained in any suitable form without limitation such as tablet, capsule, powder, granules, pellets, beads, liquid such as solution, suspension and the like. Powder, granules, pellets or beads may be filled in suitable container including sachet or hard gelatine capsules. Preferably, formulation is in the form of granules which can be either filled in a sachet or compressed to form a tablet. Most preferably, formulation is in the form of granules filled in sachet. Average particle size of said granules, as measured through sieve method, is preferably 75 to 850 microns, more preferably average particle size is 150 to 425 microns. Preferably, size of granules is no more than 1000 microns to facilitate dissolution/dispersion of granules from the formulation. Size of the granules also has significant impact on flowability of material during its formulation.

The formulation of the invention, when prepared as granules, can be administered to a mammal, after mixing it in a carrier such as water, soft food, curd, apple sauce and the like, preferably it is administered with sufficient quantity of water. Such granules may additionally comprise suspending agent, preferably povidone.

Pharmaceutical formulation according to present invention can be in the form of immediate release or controlled release formulations. Controlled release formulations may include delayed release, extended release formulation or mucoadhesive formulation. Alternatively, formulations can have mixture of immediate release or controlled release formulation.

Pharmaceutical formulation according to present invention can be prepared by any method known in the art such as by mixing the compound of formula (I), Ia or Ia' with pharmaceutically acceptable excipients. Alternatively wet granulation or dry granulation techniques may be employed for the preparation of formulation according to present invention. Selection of process of preparation of formulation according to present invention has impact on stability of compound of formula (I), Ia or Ia'. Preferably, a stable formulation is prepared by dry granulation, compaction or direct compression process, wherein water or aqueous medium is not used. Alternatively, formulation of present invention can be prepared as matrix based formulation in which compound of formula (I), Ia or Ia' is dispersed within a matrix. Alternatively, compound of formula (I), Ia or Ia' containing particles may be coated by suitable pharmaceutically acceptable carriers. Types of particles include granules, pellets, minitablets, microparticles, beads or tablets.

The formulations of the invention may also comprises adjuvant or a carrier or excipient, for example, diluent such as powdered cellulose, microcrystalline cellulose, silicified microcrystalline cellulose, starch, pre-gelatinized starch, dibasic calcium phosphate, dibasic sodium phosphate, tribasic sodium phosphate, calcium silicate, precipitated calcium carbonate; sugars such as dextrose, lactose or sucrose; sugar alcohols such as mannitol, sorbitol, xylitol, isomalt or erythritol and the like or mixture thereof; a binder such as polyvinyl alcohol, polyvinyl pyrrolidone, starch, pregelatinised starch; cellulose derivatives such as cellulose powder, microcrystalline cellulose, hydroxypropyl methylcellulose, ethyl cellulose, methyl cellulose, hydroxypropyl cellulose, hydroxyethyl cellulose, gelatin, zein, polymethacrylates, sodium alginate, gums, synthetic resins or mixture thereof; disintegrant such as calcium carboxymethyl cellulose and its salt including sodium or calcium salt, cross-linked carboxymethyl cellulose sodium (Croscarmellose sodium), cross-linked carboxymethyl cellulose calcium, cross-linked polyvinylpyrrolidone, sodium starch glycolate, pregelatinized starch, low substituted hydroxypropyl cellulose and the like or mixture thereof and/or a lubricant, for example, magnesium stearate, calcium stearate, magnesium aluminium silicate (Neusilin®), polyethylene glycol, a wax, paraffin and the like or mixture thereof. Diluent if present, is in amount of 20-90% w/w of the total formulation; disintegrant if present, is in amount of 0.1-20% w/w of total formulation; lubricant if present is in amount of 0.1-20% w/w of total formulation; binder if present, is in amount of 0.1-20% w/w of total formulation. Said formulation can optionally be coated with suitable functional or non-functional coating.

The formulation of the invention according to any of embodiment, wherein 90% of the particles of compound of formula (I), Ia or Ia' or its co-crystal are in the range from 50 microns to 1000 microns, preferably 50 microns to 700 microns, most preferably 350 microns to 600 microns, when measured through Laser diffraction method, such as Malvern Mastersizer®. Coarser particles of compound of formula (I), Ia or Ia' or its co-crystal help in improving flow property and increases its content uniformity with excipients.

When formulated as controlled release, present formulations can comprise excipient suitable for controlling the release of compound of formula (I), Ia or Ia'. Such controlled release excipient may be present either in matrix form of can be coated over particles, granules, pellets, beads, tablets or capsules.

The formulations may also contain pharmaceutically acceptable additives such as glidant, crystal growth inhibitor, film forming polymer, plasticizer, stabilizers, solubilizers, antioxidants, cosolvents, complexing agents, colouring agent, flavouring agent, sweetening agent, mucoadhesive agents and tonicity modifiers. Suitable examples and its amount are known to a person skilled in the art or as given in *Handbook of pharmaceutical excipients* (*sixth edition*, 2009). Preferably, formulation comprises sweetening agent such as sucralose and flavouring agent such as lemon flavour, Peppermint flavour, Mango Flavour or any other bitterness modifier, to mask bitter taste of the compound of formula (I).

The formulation according to present invention may be administered in combination with one or more additional therapeutic agent selected from a) antihypertensive agent; b) hypolipemic agent; c) antidiabetic agent; d) antiplatelet agent; e) anti-thrombotic agent; f) antiobesity agent; g) agent for treatment of heart failure; and h) drug for diabetic vascular complications; i) agents for cardiovascular risk reduction; or a pharmaceutically acceptable salts thereof, for treating, preventing or managing a disease selected from: diabetes and aging related macrovascular and microvascular complications including heart failure, nephrological disorder, neuropathy, atherosclerosis and retinal disorder; dermatological disorder, endothelial or other organ dysfunction and growth impairment.

Alternatively, pharmaceutical formulation according to present invention may comprise one or more additional therapeutic agent selected from a) antihypertensive agent; b) hypolipemic agent; c) antidiabetic agent; d) antiplatelet agent; e) anti-thrombotic agent; f) antiobesity agent; g) agent for treatment of heart failure; and h) drug for diabetic vascular complications; i) agents for cardiovascular risk reduction; or a pharmaceutically acceptable salts thereof.

The antihypertensive agent, as mentioned herein, includes but not limited to an angiotensin converting enzyme (ACE) inhibitor, a renin inhibitor, a beta adrenergic receptor blocker, an alpha adrenergic receptor blocker, a calcium channel blocker, a potassium channel activator, an aldosterone synthase inhibitor, a neutral endopeptidase (NEP) inhibitor, a dual angiotensin converting enzyme/neutral endopeptidase (ACE/NEP) inhibitor, an endothelin receptor antagonist, a dual angiotensin and endothelin receptor antagonist (DARA), a diuretic or a pharmaceutically acceptable salt thereof; the hypolipidemic agent or lipid-lowering agent as mentioned herein, includes but not limited to a MTP inhibitor, a HMG CoA reductase inhibitor, a squalene synthetase inhibitor, a fibric acid derivative, an ACAT inhibitor, a lipoxygenase inhibitor, a cholesterol absorption inhibitor, an ileal Na+/bile acid co-transporter inhibitor, an upregulator of LDL receptor activity, a cholesteryl ester transfer protein (CETP) inhibitor, a bile acid sequestrant, and/or nicotinic acid and derivatives or a pharmaceutically acceptable salt thereof; the antidiabetic agent, as mentioned herein, includes but not limited to a PPARγ agonist, a biguanide, a protein tyrosine phosphatase-1B (PTP-1B) inhibitor, a sulfonylurea, a meglitinide, an alpha glucoside hydrolase inhibitor, a PPARα agonist, a PPARδ agonist or antagonist, an alpha-amylase inhibitor, a fatty acid oxidation inhibitor, an A2 antagonist, a dipeptidyl peptidase IV (DP4) inhibitor, an aP2 inhibitor, a SGLT2 inhibitor, a glycogen phosphorylase inhibitor, a glucagon-like peptide-1 (GLP-1), an insulin or insulin mimetic, a PPAR.alpha./gamma dual agonist, an 11β-HSD 1 (11β-hydroxy-steroid dehydrogenase 1) inhibitor, other insulin sensitizing drug, a glucokinase activator, a VPAC2 receptor agonist or a pharmaceutically acceptable salt thereof; the antiplatelet agent as mentioned herein, includes but not limited to cyclooxygenase inhibitors, Adenosine diphosphate (ADP) receptor inhibitors, Phosphodiesterase inhibitors, Protease-activated receptor-1 (PAR-1) antagonists, Glycoprotein IIB/IIIA inhibitors, Adenosine reuptake inhibitors, Thromboxane inhibitors; the anti-thrombotic agent as mentioned herein, includes but not limited to melagatran and ximelagatran, warfarin and Factor Xa inhibitors such as rivaroxaban, apixaban, Edoxaban, razaxaban or in each case, a pharmaceutically acceptable salt thereof; an agent useful for diabetic vascular complications in present invention includes without limitation aldose reductase inhibitor, AGE inhibitor or AGE breaker. Aldose reductase inhibitor, among those suitable for the treatment of diabetic complications, represent those which decrease intracellular sorbitols by inhibiting aldose reductases, and said sorbitols accumulate excessively by enhancement of a course of polyol metabolism which is induced by continuous hyperglycemia shown in tissues developing diabetic complication; the antiobesity agent, as mentioned herein, include but not limited to a 5HT (serotonin) transporter inhibitor, a NE (norepinephrine) transporter inhibitor, a CB-1 (cannabinoind-1 receptor) antagonist/inverse agonist, a ghrelin antibody, a ghrelin antagonist, a H3 (histamine H3) antagonist/inverse agonist, a NPY1 (neuropeptide Y Y1) antagonist, a NPY2 (neuropeptide Y Y2) agonist, a NPY5 (neuropeptide Y Y5) antagonist, leptin or its derivative, an opioid antagonist, an orexin antagonist, a BRS3 (bombesin receptor subtype 3) agonist, a CCK-A (cholecystokinin-A) agonist, a CNTF (ciliary neurotrophic factor), a CNTF derivative, a GHS (growth hormone secretagogue receptor) agonist, 5HT2c (serotonin receptor 2c) agonist, a Mc3r (melanocortin 3 receptor) agonist, a Mc4r (melanocortin 4 receptor) agonist, a monoamine reuptake inhibitor, a β3 (beta adrenergic receptor 3) agonist, a DGAT1 (diacylglycerol acyltransferase 1) inhibitor, a DGAT2 (diacylglycerol acyltransferase 2) inhibitor, a FAS (fatty acid synthase) inhibitor, a PDE (phosphodiesterase) inhibitor, a thyroid hormone β agonist, an UCP-1 (uncoupling protein 1), 2, or 3 activator, an acyl-estrogen, a glucocorticoid antagonist, a SCD-1 (stearoyl-CoA desaturase-1) inhibitor, a lipase inhibitor, a fatty acid transporter inhibitor, a dicarboxylate transporter inhibitor; agents for cardiovascular risk reduction, as mentioned herein, include but not limited to the compounds as disclosed in WO2007100295, which is cited herein as reference; or pharmaceutically acceptable salts thereof.

Preferably, said additional therapeutic agent is selected from metformin, glyburide, glipizide, gliclazide, acarbose, adiposine, camiglibose, emiglitate, miglitol, voglibose, glimepiride, rosiglitazone, pioglitazone, dapagliflozin, empagliflozin, canagliflozin, alogliptin, saxagliptin, linagliptin, sitagliptin, vildagliptin, amlodipine, felodipine, nicardipine, diltiazem, lercanidipine, captopril, benazepril, quinapril, fosinopril, ramipril, enalapril, lisinopril, perindopril, aliskiren, carvedilol, metoprolol, bisoprolol, atorvastatin, simvastatin, rosuvastatin, pravastatin, fluvastatin, cerivastatin, fenofibrate, gemfibrozil, clofibrate, bezafibrate, ciprofibrate, clinofibrate, probucol, ezetimibe, aliskiren, nicorandil, clopidogrel, prasugrel, aspirin, ticlopidine, hydrochlorothiazide, rivaroxaban, indapamide, trichlormethazide, altizide, chlorthalidone, furosemide, digitoxin, digoxin, spironolectone or pharmaceutically acceptable salts thereof.

Throughout the description and claims of this specification, the words "comprise", "include" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

The term "conjugate" as used throughout the specification means compound of formula (I) Ia or Ia' is in vicinity of at least one permeation enhancer. Permeation enhancer can form complex with compound of formula (I) or Ia or Ia' or can be present in same crystal lattice to form co-crystals. Conjugate also include mixture of salt and co-crystal of compound of formula (I) or Ia or Ia' and permeation enhancer. Said conjugates are prepared by mixing compound of formula (I), Ia or Ia' with permeation enhancer, optionally in presence of base, so that permeation enhancer remains in close vicinity of compound of formula (I), Ia or Ia'. The embodiments pertaining to formulation of compound of formula (I), Ia or Ia' and method of treating using these compounds, equally apply to conjugates prepared according to present invention.

The term "co-crystals" as used herein above means that the compound of formula (I) or Ia or Ia' and at least one permeability enhancer as co-former are present in the same crystal lattice.

The phrase "a therapeutically effective amount" means the amount of compound in the formulation of present invention that, when administered to a patient for treating, preventing or managing a disease, is sufficient to effect such treatment, prevention or management for the disease.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The readers attention is directed to all papers and documents which are filed concurrently with or previous to this specification in connection with this application and which are open to public inspection with this specification, and the contents of all such papers and documents are incorporated herein by reference.

EXAMPLES

Example 1

Formulations

TABLE 1

|  | F1 % w/w | F2 % w/w | F3 % w/w |
|---|---|---|---|
| 1-(2-thien-2'-yl-2-oxo-ethyl)-3-(methanesulfonyl hydrazine carbonyl) pyridinium chloride | 25 | 25 | 39.74 |
| Light Magnesium Carbonate | 2.5 | 2.5 | — |
| Sodium caprate | 25 | 25 | 20.52 |
| Mg Aluminium trisilicate (Neusilin ® UFL2) | 1.0 | 1.0 | — |
| Mannitol 200 | — | 46.5 | — |
| Microcrystalline cellulose (Avicel 112) | 46.5 | — | 39.74 |
| Methanol | — | — | Q.S |
| Total | 100.0 | 100.0 | 100.0 |

Formulation 1(F1) and 2(F2): 2-thien-2'-yl-2-oxo-ethyl)-3-(methanesulfonyl hydrazine carbonyl) pyridinium chloride and sodium caprate were mixed in sodium hydroxide solution and dried. Obtained dried mixture was cosifted with mixture of mannitol (Formulation 1) or microcrystalline cellulose (Formulation 2) and light magnesium carbonate and mixture was blended for 5 minutes. Neusilin® was added in obtained mixture followed by co-sifting and blending for 5 minutes. Obtained mixture was dry granulated (slugging) and prepared slugs were sized through #20 mesh to obtain granules. Granules were filled in sachet.

Formulation 3(F3): 2-thien-2'-yl-2-oxo-ethyl)-3-(methanesulfonyl hydrazine carbonyl) pyridinium chloride and sodium caprate were dissolved in water and mixed to form dispersion. To the obtained dispersion, methanol was added. Obtained solution was sprayed over microcrystalline cellulose using Glatt machine. Obtained granules were compressed to form tablets.

Example 2

Assessment of Bioavailability

Bioavailability of 1-(2-thien-2'-yl-2-oxo-ethyl)-3-(methanesulfonyl hydrazine carbonyl) pyridinium compound was checked using formulations as given in Table 2.

TABLE 2

| Ingredient | F4 Qty (mg/ml) | F5 Qty (mg/ml) | F6 Qty (mg/ml) | F7 Qty (mg/ml) | F8 Qty (mg/ml) | F9 Qty (mg/ml) | F10 Qty (mg/ml) |
|---|---|---|---|---|---|---|---|
| 1-(2-thien-2'-yl-2-oxo-ethyl)-3-(methanesulfonyl hydrazine carbonyl) pyridinium chloride | 4.0 | 4.0 | 4.0 | | | | |
| Conjugate of 1-(2-thien-2'-yl-2-oxo-ethyl)-3-(methanesulfonyl hydrazine carbonyl) | | | | 7.3 | 7.9 | 7.9 | 7.9 |

TABLE 2-continued

| Ingredient | F4 Qty (mg/ml) | F5 Qty (mg/ml) | F6 Qty (mg/ml) | F7 Qty (mg/ml) | F8 Qty (mg/ml) | F9 Qty (mg/ml) | F10 Qty (mg/ml) |
|---|---|---|---|---|---|---|---|
| pyridinium chloride and sodium caprate | | | | | | | |
| Sodium caprate | 4.0 | 4.0 | | | | | |
| Magnesium carbonate light $(MgCO_3)_3 \cdot Mg(OH)_2 \cdot 3H_2O$ | | 0.05 | 0.3 | | | 0.05 | |
| $NaHCO_3$ (Sodium Bicarbonate) | | | | 4.0 | | | |
| Meglumine | | | | | 4.4 | | |
| L-Arginine | | | | | | | 0.2 |
| Hydroxy Propyl cellulose (klucel-LF) | | | | 50.0 | | 50.0 | 50.0 |
| Purified Water | Upto 1 ml | Upto 1 ml | Upto 1 ml | Upto 1 ml | Upto 1 ml | Upto 1 ml | Upto 1 ml |

Formulation 4 (F4) was prepared by co-dispensing 1-(2-thien-2'-yl-2-oxo-ethyl)-3-(methanesulfonyl hydrazine carbonyl) pyridinium chloride with sodium caprate. Purified water added and sonicated to prepare suspension. Final volume was made up with purified water. Analogous to formulation 4, formulation 5 (F5) was prepared.

Formulation 6 (F6) was prepared by dissolving light magnesium carbonate in purified water followed by dispersing 1-(2-thien-2'-yl-2-oxo-ethyl)-3-(methanesulfonyl hydrazine carbonyl) pyridinium chloride and sonication.

Formulation 7 (F7) was prepared by preparing conjugate of 1-(2-thien-2'-yl-2-oxo-ethyl)-3-(methanesulfonyl hydrazine carbonyl) pyridinium chloride and sodium caprate by dissolving 1-(2-thien-2'-yl-2-oxo-ethyl)-3-(methanesulfonyl hydrazine carbonyl) pyridinium chloride and sodium caprate using solution of sodium hydroxide and drying the solution to prepare conjugate. Said dried conjugate was added in the aq solution of $NaHCO_3$ and hydroxypropyl cellulose. Analogous to formulation 7, formulation 8 to 10 (F8-F10) were prepared.

The assessment of oral pharmacokinetics was carried out. Formulations F4 to F10 were administered orally to jugular vein cannulated Wistar rats (n=5). The blood samples were withdrawn at pre-determined time points; pre-dose (0.0 hr), 0.25, 0.5, 1, 2, 4, 6, 8, 12 and 24 hrs post dose. Plasma obtained at each time point was subjected to quantification of 1-(2-thien-2'-yl-2-oxo-ethyl)-3-(methanesulfonyl hydrazine carbonyl) pyridinium compound. LC-MS/MS method was used for the quantification of 1-(2-thien-2'-yl-2-oxo-ethyl)-3-(methanesulfonyl hydrazine carbonyl) pyridinium compound using an internal standard. The plasma samples were analyzed using solid phase extraction techniques in the calibration range of 0.500 ng/mL to 1000.000 ng/mL.

Pharmacokinetic (PK) parameters such as $C_{max}$ and AUC were calculated from concentration versus time data of 1-(2-thien-2'-yl-2-oxo-ethyl)-3-(methanesulfonyl hydrazine carbonyl) pyridinium compound using non-compartmental PK methods with the PK analysis software Phoenix WinNonlin software (version 6.3, Pharsight Corporation, USA). Data were presented with Mean±SD (standard deviation) and compared with 1-(2-thien-2'-yl-2-oxo-ethyl)-3-(methanesulfonyl hydrazine carbonyl) pyridinium compound PK data obtained after oral administration of solution of 1-(2-thien-2'-yl-2-oxo-ethyl)-3-(methanesulfonyl hydrazine carbonyl) pyridinium chloride in water under similar conditions.

The data is provided in tables 3 and 4.

TABLE 3

| Formulation | Dose | | Cmax ng/ml | AUClast hr*ng/ml |
|---|---|---|---|---|
| 1-(2-thien-2'-yl-2-oxo-ethyl)-3-(methanesulfonyl hydrazine carbonyl) pyridinium chloride | 10 mg/kg | Mean SD | 85.764 14.252 | 222.86 66.44 |
| F4 | | Mean SD | 139.885 32.028 | 265.98 35.89 |
| F5 | | Mean SD | 110.632 21.008 | 341.73 96.28 |
| F6 | | Mean SD | 119.649 43.155 | 308.56 132.22 |

Thus, use of permeability enhancing agent, in this case sodium caprate, and a base, in this case $MgCO_3$, with 1-(2-thien-2'-yl-2-oxo-ethyl)-3-(methanesulfonyl hydrazine carbonyl) pyridinium chloride increase the bioavailability. Additionally, the combination of a permeability enhancing agent and a base provides a greater boost to bioavailability of 1-(2-thien-2'-yl-2-oxo-ethyl)-3-(methanesulfonyl hydrazine carbonyl) pyridinium compound than either the permeability enhancing agent or base on their own.

Therefore, formulation according to present invention in tern increases therapeutic efficacy of compound of formula (I).

TABLE 4

| Formulation | Dose | | Cmax ng/ml | AUClast hr*ng/ml |
|---|---|---|---|---|
| 1-(2-thien-2'-yl-2-oxo-ethyl)-3-(methanesulfonyl hydrazine carbonyl) pyridinium chloride | 10 mg/kg | Mean SD | 85.764 14.252 | 222.86 66.44 |
| F7 | Equivalent to 10.0 mg/kg of 1-(2-thien-2'-yl-2-oxo-ethyl)-3-(methanesulfonyl hydrazine carbonyl) pyridinium chloride | Mean SD | 148.301 42.203 | 305.01 30.34 |
| F8 | | Mean SD | 138.356 47.667 | 397.01 222.36 |
| F9 | | Mean SD | 135.957 28.779 | 421.14 144.07 |
| F10 | | Mean SD | 146.610 47.939 | 324.55 67.44 |

Table 4 shows that improved bioavailability is still observed when the permeability enhancing agent and 1-(2- thien-2'-yl-2-oxo-ethyl)-3-(methanesulfonyl hydrazine carbonyl) pyridinium chloride are formulated as the conjugate.

Example 3

Formulations

| Ingredients | F11 % w/w | F12 % w/w | F13 % w/w |
|---|---|---|---|
| Conjugate of 1-(2-thien-2'-yl-2-oxo-ethyl)-3-(methanesulfonyl hydrazine carbonyl) pyridinium chloride and sodium caprate | 41.67 | 41.67 | 42.37 |
| Magnesium carbonate light $(MgCO_3)_3*Mg(OH)_2*3H_2O$ | 2.08 | 2.08 | 2.12 |
| Mg Aluminium trisilicate (Neusilin ® UFL2) | 0.83 | 0.83 | 0.85 |
| Mannitol | 38.75 | 38.75 | 39.41 |
| Sucralose | 6.67 | 6.67 | 6.78 |
| Povidone K30 | 3.33 | 3.33 | 3.39 |
| Lemon Flavour | 2.08 | 2.08 | 2.12 |
| Peppermint Flavour | 4.17 | 4.17 | 2.12 |
| Mango Maracuja | — | 0.42 | 0.42 |
| Bitterness Modifier from IFF | 0.42 | — | 0.42 |
| Total | 100.00 | 100.00 | 100.00 |

Mannitol, magnesium carbonate light were cosifted through #20 mesh. Conjugate of 1-(2-thien-2'-yl-2-oxo-ethyl)-3-(methanesulfonyl hydrazine carbonyl) pyridinium chloride and sodium caprate was separately cosifted with Mg Aluminium trisilicate through #20 mesh. and mixed with cosifted mannitol and magnesium carbonate light. Obtained mixture was blended for 10 minutes in Conta blender and then subjected to roller compaction to prepare granules, followed by sizing by using quadro mill. Obtained granules were mixed with povidone, sucralose, lemon flavour, peppermint flavour, Mango Maracuja (In F12 and F13) and Bitterness modifier (In F11, and F13) in Conta blender and obtained material was filled in the sachet.

The invention claimed is:

1. An oral pharmaceutical formulation comprising a compound of formula (I):

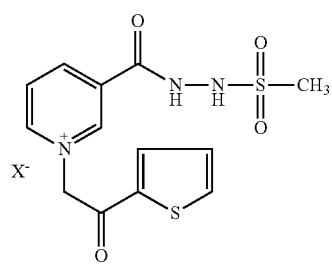

or its co-crystal; wherein the compound of formula (I) or its co-crystal is present in an amount from about 0.1% to about 80% w/w of total formulation;
wherein $X^-$ is a carboxylate ion or $X^-$ is a halide;
a permeability enhancing agent selected from the group consisting of sodium caprylate, sodium caprate, sodium laurate and sodium oleate, wherein the permeability enhancing agent is present in an amount of from about 0.02% to about 75% w/w of total formulation; and
a base selected from the group consisting of organic base, inorganic base, phosphate buffer, and salt of a carboxylic acid comprising less than 5 carbon atoms, wherein the base is present in an amount of from about 0.002% to about 60% w/w of total formulation;
and optionally a pharmaceutically acceptable excipient selected from the group consisting of a sweetening agent, diluent, binder, lubricant, and mixtures thereof; wherein said formulation exhibits increased oral bioavailability of compound of formula (I).

2. The formulation according to claim 1, wherein $X^-$ is chloride or caprate.

3. The formulation according to claim 1, wherein the permeability enhancing agent is sodium caprate.

4. The formulation according to claim 1, wherein the base is an inorganic base.

5. The formulation according to claim 4, wherein the inorganic base is magnesium carbonate.

6. The formulation according to claim 1, wherein the formulation comprises from 150 mg to 1500 mg of the compound of formula (I) or its co-crystal.

7. The formulation according to claim 6, wherein the formulation comprises from 250 mg to 750 mg of the compound of formula (I) or its co-crystal.

8. The formulation according to claim 1, wherein the permeability enhancing agent is present in an amount from about 2.5% to about 60% w/w of total formulation.

9. The formulation according to claim 1, wherein the permeability enhancing agent is present in an amount from about 5% to about 30% w/w of total formulation.

10. The formulation according to claim 1, wherein the base is present in an amount from about 0.2% to about 25% w/w of total formulation.

11. The formulation according to claim 1, wherein the base is present in an amount from about 0.5% to about 15.0% w/w of total formulation.

12. The formulation according to claim 1, wherein the base is present in an amount from about 0.5% to about 5% w/w of total formulation.

13. The formulation according to claim 1, wherein the compound of formula (I) or its co-crystal is present in an amount from about 0.25% to about 70% w/w of total formulation.

14. The formulation according to claim 1, wherein the compound of formula (I) or its co-crystal is present in an amount from about 5% to about 50% w/w of total formulation.

15. An oral pharmaceutical formulation comprising a compound of formula (I):

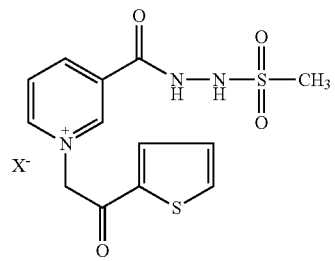

or its co-crystal, wherein the compound of formula (I) or its co-crystal is present in an amount from about 0.1% to about 80% w/w of total formulation;

wherein X⁻ is a carboxylate ion or X⁻ is a halide;

a permeability enhancing agent selected from the group consisting of sodium caprylate, sodium caprate, sodium laurate and sodium oleate, wherein the permeability enhancing agent is present in an amount of from about 0.02% to about 75% w/w of total formulation; and a base selected from the group consisting of organic base, inorganic base, phosphate buffer and salt of carboxylic acid comprising less than 5 carbon atoms, wherein the base is present in an amount of from about 0.002% to about 60% w/w of total formulation;

optionally a pharmaceutically acceptable excipient selected from the group consisting of a sweetening agent, diluent, binder, lubricant, and mixtures thereof;

wherein said formulation exhibits increased oral bioavailability of compound of formula (I), wherein the compound of formula (I) and the permeability enhancing agent are in the form of conjugate.

16. The formulation according to claim 15, wherein X⁻ is chloride or caprate.

17. The formulation according to claim 15, wherein the permeability enhancing agent is sodium caprate.

18. The formulation according to claim 15, wherein the base is an inorganic base.

19. The formulation according to claim 18, wherein the inorganic base is selected from the group consisting of sodium carbonate, sodium bicarbonate, potassium carbonate, potassium bicarbonate, calcium carbonate, magnesium carbonate, and magnesium bicarbonate.

20. The formulation according to claim 15, wherein the base is an organic base selected from arginine, lysine, histidine, meglumine, and glucosamine.

21. The formulation according to claim 4, wherein the inorganic base is selected from the group consisting of sodium carbonate, sodium bicarbonate, potassium carbonate, potassium bicarbonate, calcium carbonate, magnesium carbonate, and magnesium bicarbonate.

22. The formulation according to claim 1, wherein the base is an organic base selected from arginine, lysine, histidine, meglumine, and glucosamine.

23. The oral pharmaceutical formulation according to claim 15, wherein the formulation further comprises a sweetening agent.

24. The oral pharmaceutical formulation of claim 23, wherein the compound of formula (I) or its co-crystal is present in an amount from about 0.25% to about 70% w/w of total formulation; the permeability enhancing agent is present in an amount of from about 2.5% to about 60% w/w of total formulation; and the base is present in an amount of from about 0.2% to about 25% w/w of total formulation.

* * * * *